US009173649B2

(12) United States Patent
Clark et al.

(10) Patent No.: US 9,173,649 B2
(45) Date of Patent: Nov. 3, 2015

(54) LOW PROFILE DISTRACTOR APPARATUSES

(75) Inventors: Andrew Clark, Arlington, MA (US); David Chella, Brighton, MA (US); Jesse Drake, Westborough, MA (US)

(73) Assignee: Allen Medical Systems, Inc., Batesville, IN (US)

( * ) Notice: Subject to any disclaimer, the term of this patent is extended or adjusted under 35 U.S.C. 154(b) by 330 days.

(21) Appl. No.: 13/435,022

(22) Filed: Mar. 30, 2012

(65) Prior Publication Data
US 2012/0259343 A1 Oct. 11, 2012

Related U.S. Application Data

(60) Provisional application No. 61/473,386, filed on Apr. 8, 2011.

(51) Int. Cl.
| A61B 17/02 | (2006.01) |
| A61B 17/60 | (2006.01) |
| A61B 17/66 | (2006.01) |
| A61F 5/042 | (2006.01) |
| A61F 5/04 | (2006.01) |
| A61F 5/37 | (2006.01) |

(52) U.S. Cl.
CPC ............... *A61B 17/025* (2013.01); *A61B 17/60* (2013.01); *A61B 17/66* (2013.01); *A61F 5/04* (2013.01); *A61F 5/042* (2013.01); *A61F 5/3776* (2013.01); *A61B 2017/0268* (2013.01); *A61B 2017/0275* (2013.01)

(58) Field of Classification Search
CPC ............. A61B 17/025; A61B 17/2804; A61B 2017/0256; A61B 2017/0268; A61B 2017/0275; A61B 17/60; A61B 17/66; A61F 5/04; A61F 5/042

USPC ............................................ 606/90, 105, 241
See application file for complete search history.

(56) References Cited

U.S. PATENT DOCUMENTS 1,837,037 A * 12/1931 Gillberg ......................... 602/33
1,890,372 A * 12/1932 Ettinger ......................... 602/35
2,198,908 A 4/1940 Ellis
(Continued)

FOREIGN PATENT DOCUMENTS

GB 2080113 A 2/1982
WO 01/45601 A2 6/2001

OTHER PUBLICATIONS

Extended European Search Report, Aug. 13, 2012.
(Continued)

*Primary Examiner* — Larry E Waggle, Jr.
(74) *Attorney, Agent, or Firm* — Dinsmore & Shohl LLP

(57) ABSTRACT

Embodiments of low profile distractor apparatuses are disclosed. The distractor apparatuses generally comprise a mounting body, a tensioning mechanism coupled to the mounting body and a distractor arm coupled to the tensioning mechanism and pivotally coupled to the mounting body for rotation relative to the mounting body. The tensioning axis of the tensioning mechanism is non-coaxial with an effector axis of the distractor arm and a distraction force applied with the distractor arm is translated to the effector axis. This enables the distractor apparatus to be positioned relative to a patient such that the tensioning mechanism is offset from the long axis of the limb of the patient thereby facilitating improved access to the distal portions of the limb.

18 Claims, 15 Drawing Sheets

(56) References Cited

U.S. PATENT DOCUMENTS

| | | | |
|---|---|---|---|
| 2,511,182 A | 6/1950 | Spencer | |
| 2,644,448 A | 7/1953 | Jardine | |
| 2,723,663 A | 11/1955 | Davis | |
| 3,135,257 A | 6/1964 | Anderson | |
| 3,385,292 A | 5/1968 | Hardy | |
| 3,477,428 A | 11/1969 | Hare | |
| 3,612,046 A | 10/1971 | Gaylord | |
| 3,618,598 A | 11/1971 | Davis | |
| 3,680,551 A | 8/1972 | Bell et al. | |
| 3,680,552 A | 8/1972 | Bell et al. | |
| 3,720,206 A | 3/1973 | Walker et al. | |
| 3,750,652 A * | 8/1973 | Sherwin | 606/90 |
| 3,978,853 A | 9/1976 | Morrison | |
| 4,144,880 A | 3/1979 | Daniels | |
| 4,265,230 A | 5/1981 | Jordon | |
| 4,350,153 A | 9/1982 | Borschneck | |
| 4,443,005 A | 4/1984 | Sugarman et al. | |
| 4,573,482 A | 3/1986 | Williams | |
| 5,020,525 A | 6/1991 | Ewing et al. | |
| 5,025,802 A | 6/1991 | Laico et al. | |
| 5,027,799 A | 7/1991 | Laico et al. | |
| 5,063,918 A | 11/1991 | Guhl | |
| 5,100,129 A | 3/1992 | Porter et al. | |
| 5,162,039 A | 11/1992 | Dahners | |
| 5,290,220 A | 3/1994 | Guhl | |
| 5,608,934 A | 3/1997 | Torrie et al. | |
| 5,743,898 A | 4/1998 | Bailey et al. | |
| 5,899,901 A * | 5/1999 | Middleton | 606/914 |
| 5,967,947 A | 10/1999 | Glover | |
| 6,629,944 B2 | 10/2003 | Smart | |
| 6,712,825 B2 * | 3/2004 | Aebi et al. | 606/90 |
| 6,716,218 B2 * | 4/2004 | Holmes et al. | 606/105 |
| 6,953,443 B2 | 10/2005 | Hay | |
| 7,097,647 B2 * | 8/2006 | Segler | 606/90 |
| 7,100,296 B2 | 9/2006 | Root | |
| 7,131,955 B2 | 11/2006 | Price et al. | |
| 7,243,654 B2 | 7/2007 | Schuerch | |
| 7,244,238 B2 | 7/2007 | March et al. | |
| 7,452,343 B2 | 11/2008 | Campbell | |
| 7,641,624 B2 | 1/2010 | Kendrick | |
| 7,771,378 B2 | 8/2010 | Price et al. | |
| 7,832,401 B2 | 11/2010 | Torrie et al. | |
| 7,857,780 B2 | 12/2010 | Sommers et al. | |
| 7,947,006 B2 | 5/2011 | Torrie et al. | |
| 7,947,862 B2 | 5/2011 | Livorsi | |
| 8,083,746 B2 * | 12/2011 | Novak | 606/88 |
| 2002/0128577 A1 | 9/2002 | Smart | |
| 2004/0015114 A1 | 1/2004 | Hay | |
| 2004/0039397 A1 * | 2/2004 | Weber et al. | 606/90 |
| 2004/0167455 A1 | 8/2004 | Smart | |
| 2005/0177173 A1 * | 8/2005 | Aebi et al. | 606/105 |
| 2006/0004380 A1 * | 1/2006 | DiDomenico et al. | 606/105 |
| 2006/0224096 A1 | 10/2006 | Lott | |
| 2007/0265635 A1 | 11/2007 | Torrie et al. | |
| 2008/0103425 A1 | 5/2008 | Berlet | |
| 2008/0287995 A1 * | 11/2008 | Gauthier | 606/246 |
| 2010/0249788 A1 * | 9/2010 | Roche | 606/87 |
| 2011/0106094 A1 * | 5/2011 | Mitchell | 606/90 |
| 2011/0190676 A1 | 8/2011 | Torrie et al. | |

OTHER PUBLICATIONS

Innomed, Inc., "Shereff Ankle Distractor" and "Strap for Shereff Ankle Distractor", 2011.
Smith & Nephew, Inc., "Acufex® Non-Invasive Ankle Distractor", Nov. 22, 1999.
Arthrocare Sports Medicine, "Ankle Distraction for Arthroscopic Surgery", 2007.

* cited by examiner

LOW PROFILE DISTRACTOR APPARATUSES

CROSS REFERENCE TO RELATED APPLICATIONS

The present application claims priority to U.S. Provisional Patent Application Ser. No. 61/473,386 filed Apr. 8, 2011 and entitled "LOW PROFILE DISTRACTOR APPARATUSES," the entirety of which is incorporated herein by reference.

TECHNICAL FIELD

The present specification generally relates to apparatuses for limb distraction and, more specifically, to low profile distractors for applying tension to a limb, such as a leg, during medical procedures.

BACKGROUND

Surgical procedures performed on a joint, such as an ankle, often require distraction or spreading of the joint to facilitate the insertion and manipulation of surgical implements in the joint. Conventional distractor apparatuses are generally axially aligned with the limb in which the joint resides such that tension can be applied to the limb thereby spreading or decompressing the joint. The distractor apparatus may exert the tension on the limb via a strap which is attached to both the distractor and the limb. For instance, where surgery is being performed on an ankle, the distractor apparatus is aligned with the long axis of the lower leg and a strap is attached to the foot and/or ankle. Tension may be applied to the leg and ankle by rotating a worm screw of the distractor apparatus which is attached to the strap. In such apparatuses the long axis of the worm screw is generally aligned with the long axis of the lower leg such that the worm screw and the lower leg are substantially coaxial.

Such conventional distractor apparatus designs have several drawbacks. For instance, achieving the magnitude of tension necessary to adequately decompress the joint may be difficult for an operator to obtain by manual manipulation of the worm screw. Moreover, because the distractor apparatus must be axially aligned with the long axis of the limb to facilitate application of the distraction force, the distractor apparatus takes up a significant amount of space distal to the foot thereby hindering access to the joint of interest and increasing the difficulty of performing the surgical operation.

Accordingly, a need exists for alternative distractor apparatuses which facilitate improved access to the extremities of a distracted limb.

SUMMARY

In one embodiment, a distractor apparatus may include a mounting body and a tensioning mechanism coupled to the mounting body. A distractor arm may be coupled to the tensioning mechanism and pivotally coupled to the mounting body for rotation relative to the mounting body. Rotation of the tensioning mechanism applies a distraction force on the distractor arm and a tensioning axis of the tensioning mechanism is non-coaxial with an effector axis of the distractor arm. The distraction force applied to the distractor arm with the tensioning mechanism is translated from the tensioning axis to the effector axis through the distractor arm.

In another embodiment, a distractor apparatus for applying a distraction force to a limb of a patient may include a mounting body comprising a body yoke and a frame coupled to the mounting body. The frame may include at least one pivot nut positioned in the frame such that the at least one pivot nut is pivotable with respect to the frame. A tensioning mechanism may be threadably engaged with the at least one pivot nut. The tensioning mechanism may include a threaded rod having a control knob positioned on one end and a rod yoke positioned on an opposite end. A distractor arm may include a receiving hook disposed in a free end of the distractor arm. A first end of the distractor arm opposite the free end may be pivotally coupled to the rod yoke and the body yoke is pivotally coupled to the distractor arm between the free end and the first end. Rotation of the tensioning mechanism pivots the distractor arm in the body yoke with respect to the mounting body such that the distraction force applied along a tensioning axis of the tensioning mechanism is translated through the distractor arm to an effector axis of the distractor arm, wherein the tensioning axis is non-coaxial with the effector axis.

In yet another embodiment, a distractor apparatus for applying a distraction force to a limb of a patient may include a mounting body comprising a body yoke and a pivot nut positioned in the mounting body and pivotable with respect to the mounting body. A tensioning mechanism may be threadably engaged with the pivot nut. The tensioning mechanism may include a threaded rod having a control knob positioned on one end and a rod yoke positioned on an opposite end. The distractor apparatus may further include a receiving hook disposed in a free end. A first end of the distractor arm opposite the free end may be pivotally coupled to the rod yoke and the body yoke may be pivotally coupled to the distractor arm between the first end and the free end. Rotation of the tensioning mechanism rotates the distractor arm in the body yoke thereby pivoting the distractor arm with respect to the mounting body such that the distraction force applied along a tensioning axis of the tensioning mechanism is translated to an effector axis of the distractor arm through the distractor arm, wherein the tensioning axis is non-coaxial with the effector axis.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIGS. 12A-12I schematically depict alternative embodiments of distractor apparatuses which utilize a distractor arm pivoted about a pivot point to apply tension to a limb.

DETAILED DESCRIPTION

Figure 1:
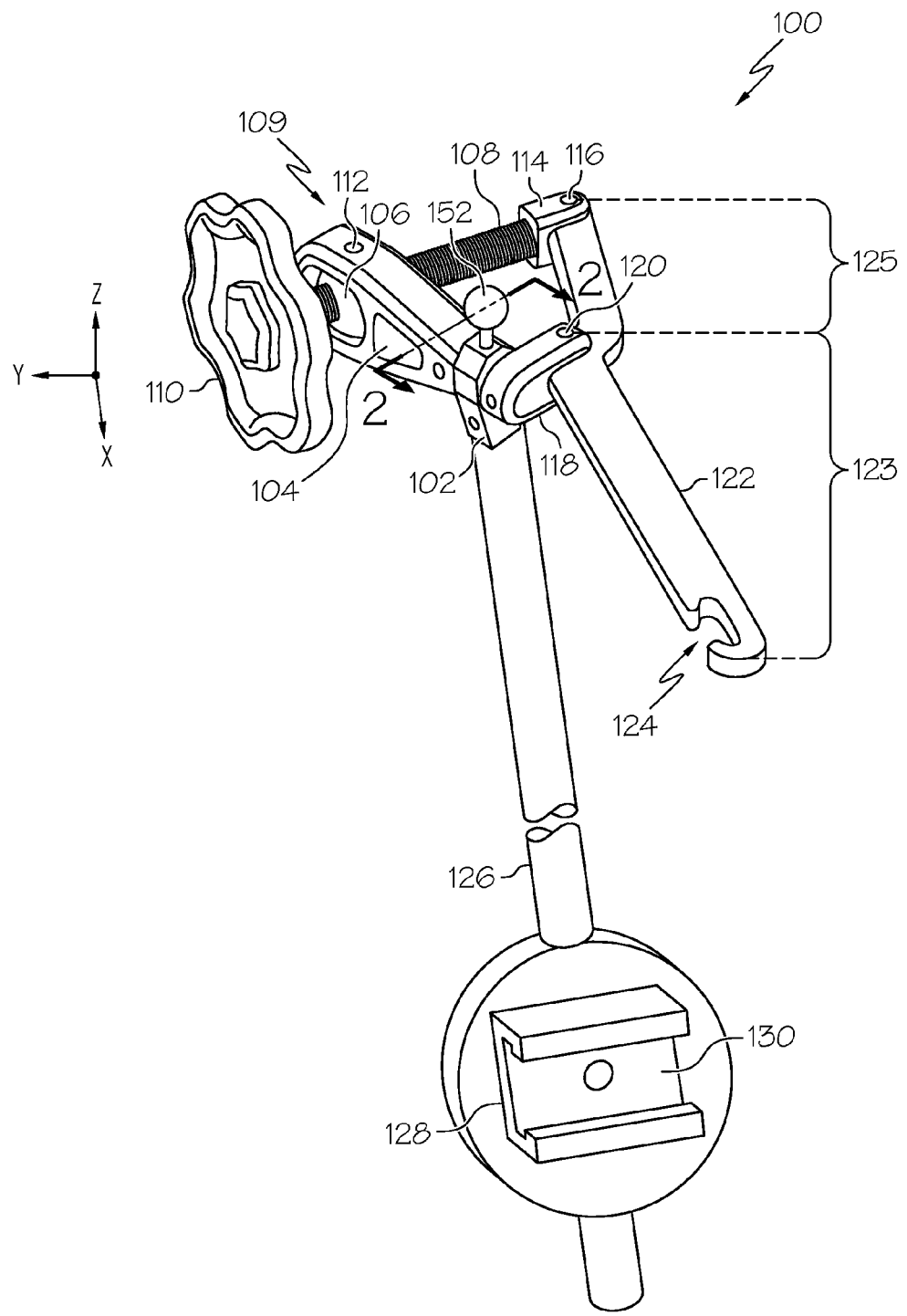
FIG. 1 schematically depicts a distractor apparatus according to one or more embodiments shown and described herein.

FIG. 1 generally depicts one embodiment of a distractor apparatus for applying tension to a limb of a patient, such as a leg. The distractor apparatus generally comprises a mounting body, a frame, a tensioning mechanism, and a distractor arm with a receiving hook. The tensioning mechanism and the distractor arm are pivotally coupled to the frame such that actuation of the tensioning mechanism pivots the distractor arm relative to the frame such that tension may be applied to or released from a limb coupled to the receiving hook of the distractor arm with a strap or another accessory. Various embodiments of the distractor apparatus and methods for using the distractor apparatus will be described in more detail herein with specific reference to the appended drawings.

Referring now to FIG. 1, a distractor apparatus 100 is schematically depicted according to one or more embodiments shown and described herein. The distractor apparatus 100 generally comprises a mounting body 102, a frame 104, a tensioning mechanism 109 and a distractor arm 122. The mounting body 102 is disposed on a first end of a support 126 which, in the embodiment shown in FIG. 1, is a cylindrical rod. The second end of the support 126 is coupled to a connector 128 with a slot 130 to facilitate coupling the distractor apparatus 100 to an accessory rail (not shown) attached to a piece of medical equipment (not shown) such as, for example, a hospital bed or operating table. The support 126 is coupled to the connector 128 such that the support 126 is capable of rotation relative to the connector 128.

The frame 104 and a body yoke 118 are rotatably coupled to the mounting body 102 with an axle (not shown) which extends from the frame 104, through the mounting body 102 and into the body yoke 118. Accordingly, it should be understood that the frame 104 and body yoke 118 are rotatable with respect to the mounting body 102. In one embodiment (not shown), the axle is integrally formed with at least one of the frame 104 or the body yoke 118. In another embodiment, the axle is a separate component which is positioned in bores (not shown) formed in the frame 104 and the body yoke 118 and secured with set screws. The mounting body 102 may further comprise one or more bearings (not shown) through which the axle extends to facilitate rotation of the frame 104 and body yoke 118 relative to the mounting body 102.

Rotation of the frame 104 and body yoke 118 with respect to the mounting body 102 facilitates maintaining the general orientation of the distractor apparatus 100 with respect to an attached limb (such as the leg of a patient or the like) while exerting a gross distraction force on the attached limb by rotating the support 126 with respect to the connector. In one embodiment, rotation of the frame 104 and the body yoke 118 with respect to the mounting body 102 controlled utilizing a set screw attached to knob 152. Specifically, the knob 152 may be used to impinge a set screw against the axle extending through the mounting body 102 thereby preventing rotation of the frame 104 and body yoke 118 with respect to the mounting body 102 once the desired position is achieved.

Figure 2:
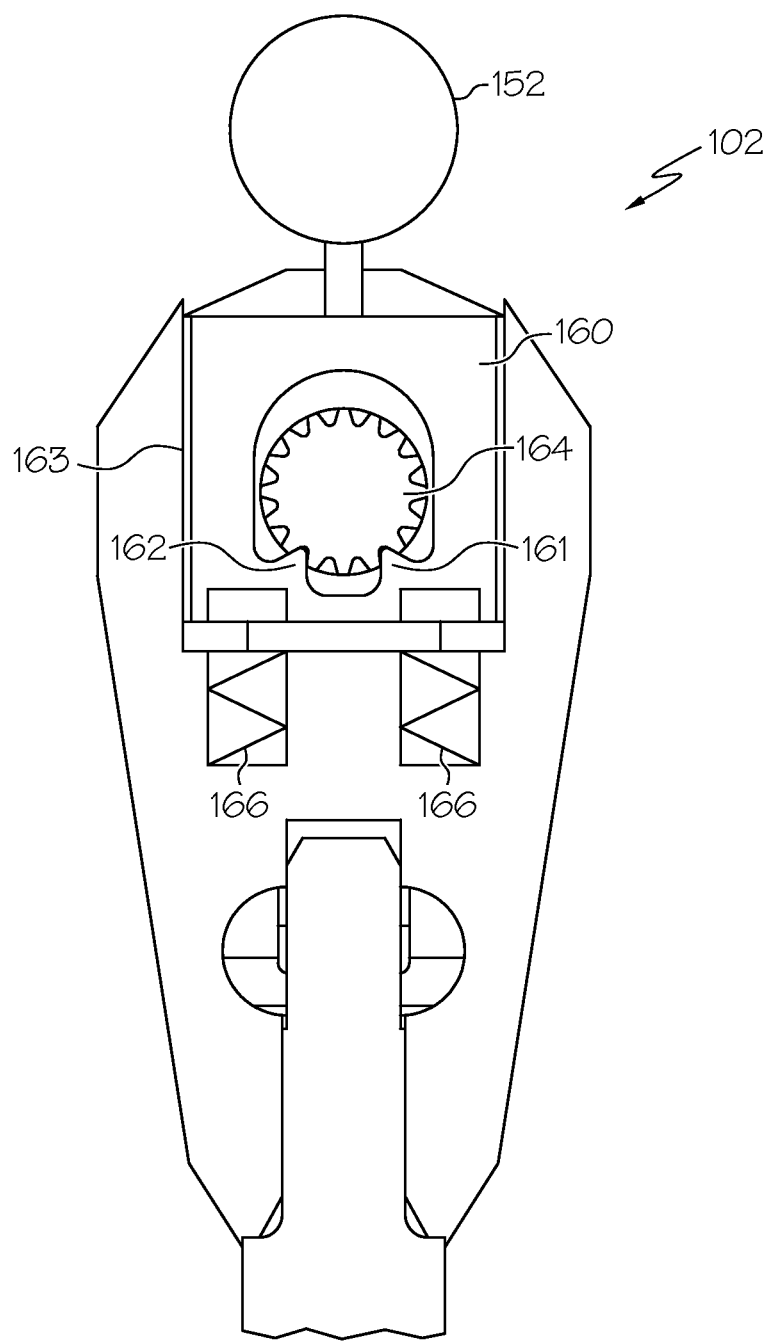
FIG. 2 schematically depicts one embodiment of a mounting body of a distractor apparatus.

Referring now to FIG. 2, in another embodiment, rotation of the frame 104 and the body yoke 118 is controlled utilizing a keeper 160 in conjunction with grooves formed in the axle 164. For example, the keeper 160 may be positioned in a slot 163 formed in the mounting body 102 with springs 166 biasing the keeper 160 into engagement with the axle 164. Specifically, as the keeper 160 is biased out of the mounting body 102, a pair of lobes 161, 162 engage with the grooves formed in the axle 164 preventing rotation of the axle with respect to the mounting body 102 and, as such, preventing the rotation of the frame 104 and the body yoke 118 with respect to the mounting body 102. The knob 152 may be coupled to the keeper such that depressing the knob 152 disengages the keeper 160 from the axle 164 thereby permitting rotation of the axle 164 with respect to the mounting body 102.

Referring again to FIG. 1, the frame 104 extends from the mounting body 102 such that the frame is generally at a right angle with respect to the support 126. The frame 104 is formed with at least one opening in which a pivot nut 106 is positioned. Specifically, the pivot nut 106 is disposed in the frame 104 and secured with pivot pins 112 (one shown in FIG. 1) such that the pivot nut 106 is free to rotate with respect to the frame 104 while being secured to the frame 104.

The tensioning mechanism 109 generally comprises a threaded rod 108, a control knob 110 and a rod yoke 114. The threaded rod 108 is threaded through the pivot nut 106 of the frame 104 such that a portion of the threaded rod 108 extends from either side of the frame. The control knob 110 is secured to a first end of the threaded rod 108 and the rod yoke 114 is secured to the second end of the threaded rod 108.

The distractor arm 122 is an elongated lever comprising a first portion 123 and a second portion 125. In the embodiments described herein the first portion 123 of the distractor arm 122 is generally longer than the second portion 125 of the distractor arm 122 to increase the range of travel and the torque applied to the receiving hook 124 with the tensioning mechanism 109. The receiving hook 124 is formed at the free end of the first portion 123 of the distractor arm 122 to facilitate attaching one or more accessories, such as a tensioning strap, tension gauge, or the like, to the distractor arm 122. The distractor arm 122 is pivotally coupled to the rod yoke 114 and the body yoke 118 such that the receiving hook 124 is pivotable with respect to the mounting body 102. Specifically, the body yoke 118 is coupled to the distractor arm 122 with pivot pin 120 such that the distractor arm 122 is pivotable about the pivot pin 120. Similarly, the rod yoke 114 is coupled to the second portion 125 of the distractor arm 122 with pivot pin 116. In the embodiments shown herein, the first portion 123 of the distractor arm 122 transitions into the second portion 125 of the distractor arm 122 proximate the pivot pin 120 coupling the distractor arm 122 to the body yoke 118. In the embodiment of the distractor apparatus 100 depicted in FIG. 1 the distractor arm 122 is coupled to the body yoke 118 and the rod yoke 114 such that the distractor arm 122 is substantially horizontally oriented (i.e., the distractor arm is within +/−10 degrees from parallel with the x-y plane of the coordinate axes of FIG. 1). Accordingly, it should be understood that the distractor arm 122 is pivotable with respect to the mounting body 102 in the x-y plane of the coordinate axes of FIG. 1.

Figure 3:
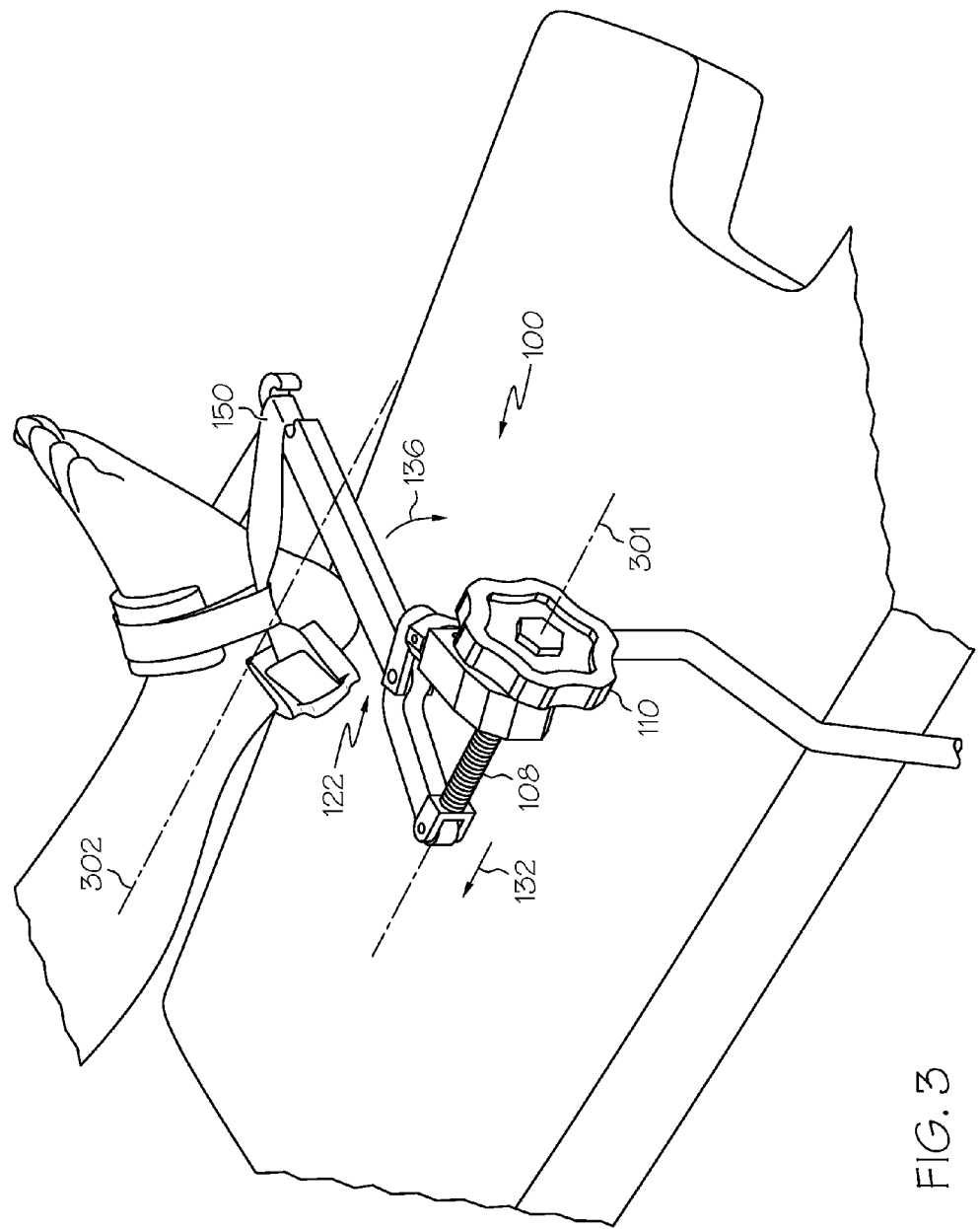
FIG. 3 schematically depicts the distractor apparatus of FIG. 1 being used to apply a distraction force to a limb of a patient.

The operation of the distractor apparatus 100 will now be described with specific reference to FIGS. 3-5.

In describing the function of the distractor apparatus 100 reference will be made to strap 150 which is shown attached to the ankle of a patient in FIG. 3 and partially depicted in FIGS. 4 and 5. A first portion of the strap 150 is received in the receiving hook 124 of the distractor arm 122 as depicted in FIG. 3 such that a tension may be applied to the strap 150 or a tension released from the strap 150 by rotation of the distractor arm 122 about the pivot pin 120. A second end (not shown) of the strap 150 may be attached to a limb of a patient which is constrained either with a device or by the weight of the patient. For example, in one embodiment the distractor apparatus 100 is an ankle distractor and the strap is attached to an ankle of a patient to apply a distraction force to the leg which is counteracted by the leg being positioned in a urology leg holder.

Figure 4:
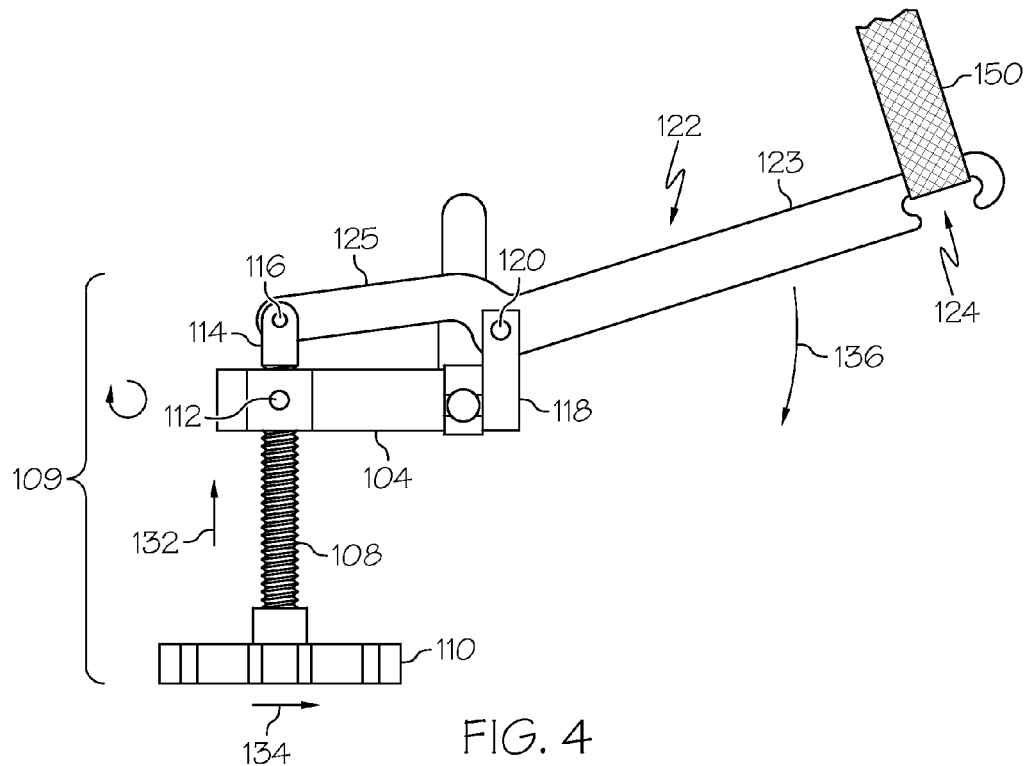
FIG. 4 schematically depicts the distractor apparatus of FIG. 3 being used to apply tension to a strap attached to the distractor apparatus.

Referring to FIG. 4, a distracting force may be applied to the strap 150 by actuating the tensioning mechanism 109 with control knob 110. Specifically, rotating the control knob 110 in a tensioning direction (which is the clockwise direction indicated by arrow 134 in this example) causes the threaded rod 108 to rotate in the pivot nut thereby advancing the threaded rod 108 in the direction indicated by arrow 132. As the threaded rod 108 advances it exerts a force on the distractor arm 122 through the rod yoke 114. The force applied to the distractor arm 122 causes the distractor arm 122 to rotate in a clockwise direction in the body yoke 118 about the pivot pin 120 which, in turn, causes the receiving hook 124 of the distractor arm 122 to advance in the direction generally indicated by arrow 136, thereby applying a distraction force to the strap 150 and to the limb attached to the strap.

As the distractor arm 122 is rotated about the pivot pin 120, the distractor arm 122 also rotates in the rod yoke 114 about the pivot pin 116 to accommodate for the rotation of the distractor arm. Moreover, as the distractor arm 122 rotates in the clockwise direction, the distractor arm exerts a torque on the threaded rod 108 causing the threaded rod 108 and the pivot nut 106 (not shown in FIG. 4) to rotate in the frame 104 about the pivot pin 112 in a clockwise direction. The ability to rotate the threaded rod 108 and the pivot nut 106 in the frame 104 increases the maximum amount of travel of the threaded rod 108 as well as the amount of rotation of the distractor arm 122. FIG. 5 generally depicts the threaded rod 108 and the distractor arm 122 at maximum displacement when applying a distraction force to the strap.

Figure 5:
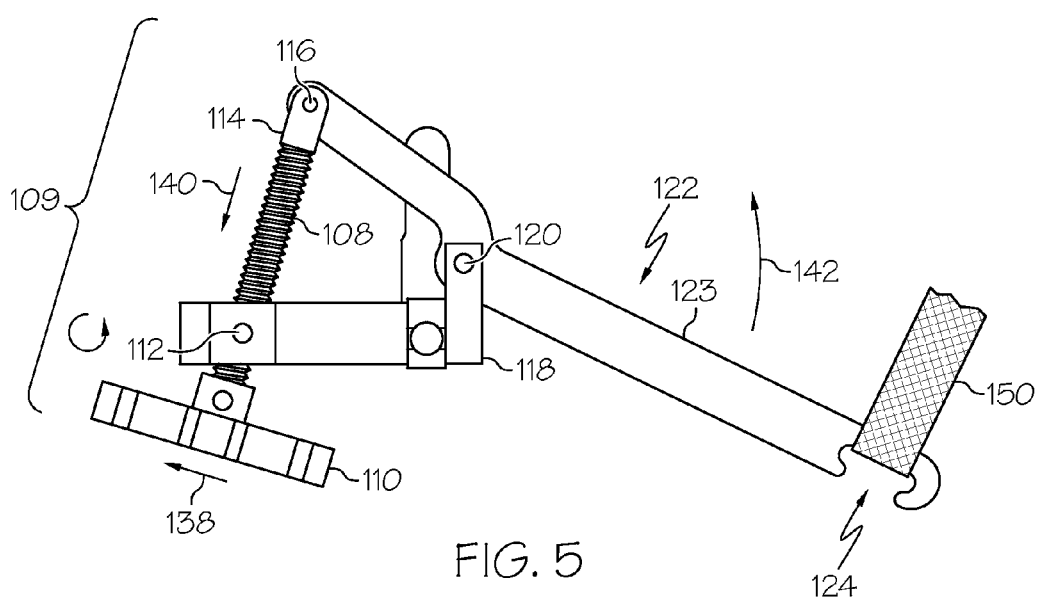
FIG. 5 schematically depicts the distractor apparatus of FIG. 3 being used to release tension applied to a strap attached to the distractor apparatus.

Referring to FIG. 5, the distraction force applied to the strap 150 with the distractor apparatus 100 can be released by reversing the operation described above. Specifically, rotating the control knob 110 in a slack direction (which is the counter-clockwise direction indicated by arrow 138 in this example) causes the threaded rod 108 to rotate in the pivot nut thereby advancing the threaded rod 108 in the direction indicated by arrow 140. As the threaded rod 108 advances it exerts a force on the distractor arm 122 through the rod yoke 114. The force applied to the distractor arm 122 causes the distractor arm 122 to rotate in a counter-clockwise direction in the body yoke 118 about the pivot pin 120 which, in turn, causes the receiving hook 124 of the distractor arm 122 to advance in the direction generally indicated by arrow 142, thereby releasing the tension applied to the strap 150 and relaxing the distracting force to the limb attached to the strap.

As the distractor arm 122 is rotated about the pivot pin 120, the distractor arm 122 also rotates in the rod yoke 114 about the pivot pin 116 to accommodate for the rotation of the distractor arm in a direction which is generally opposite the direction of advance of the threaded rod 108. Moreover, as the distractor arm 122 rotates in the counter-clockwise direction, the distractor arm exerts a torque on the threaded rod 108 causing the threaded rod 108 and the pivot nut 106 (not shown in FIG. 5) to rotate in the frame 104 about the pivot pin 112 in a counter-clockwise direction. The control knob 110 may be rotated in the slack direction until a sufficient amount of slack is generated in the strap 150 and/or until the threaded rod reaches the maximum extent of travel in the direction of arrow 140.

Figure 11:
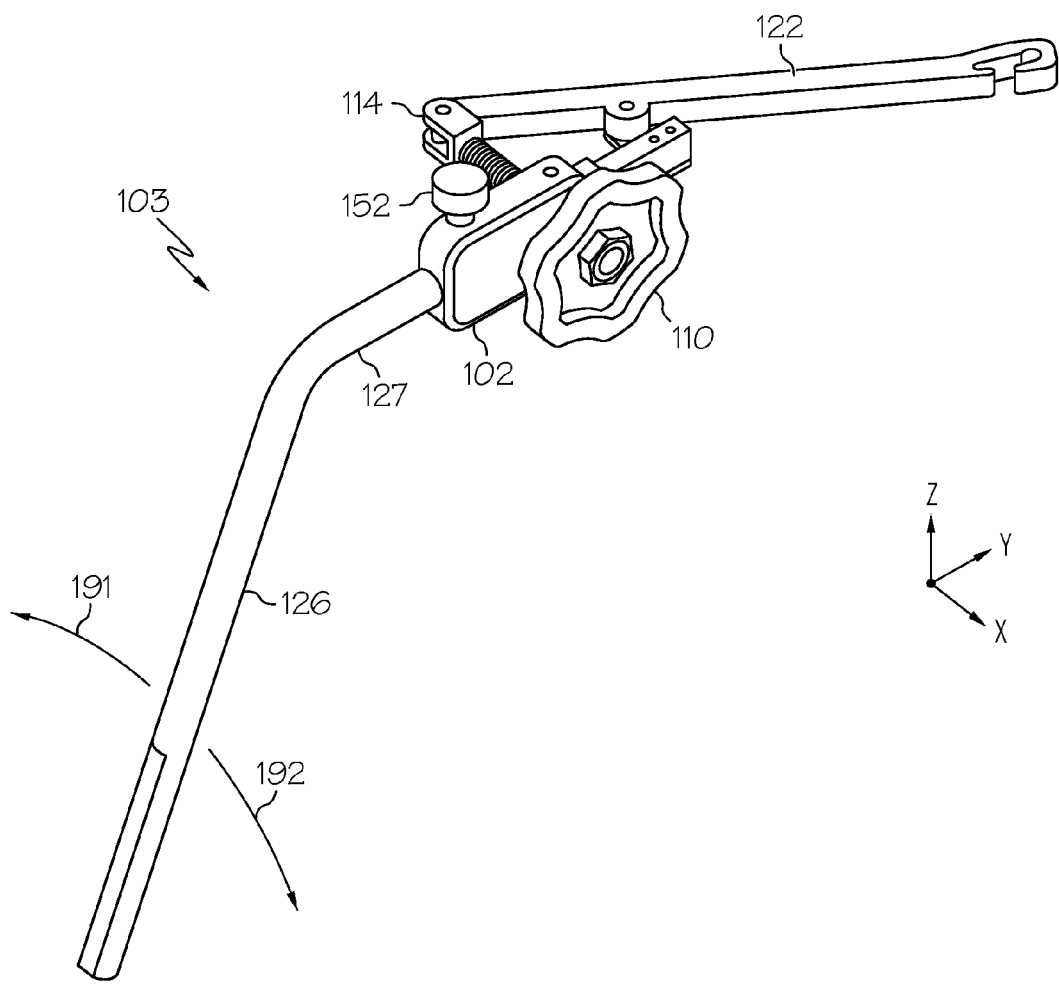
FIG. 11 schematically depicts an alternative embodiment of a distractor apparatus.

While FIGS. 1-5 generally depict one embodiment of a distractor apparatus 100, it should be understood that other embodiments of the distractor apparatus are contemplated. For example, FIG. 11 depicts another embodiment of a distractor apparatus 103 in which the distractor arm 122 is substantially horizontally oriented. In this embodiment the tensioning mechanism (i.e., the threaded rod 108, control knob 110, and pivot nut) is positioned in the mounting body 102 (as opposed to the frame as in the embodiment depicted in FIG. 1). In this embodiment the support 126 includes an angled extension 127 such that the mounting body 102 is cantilevered. The mounting body 102 is rotatable on the angled extension 127 such that the horizontal orientation of the distractor arm 122 can be maintained when the support 126 is pivoted in the direction of arrow 191 or arrow 192. The mounting body 102 may be fixed in place on the angled extension 127 with knob 152 coupled to a set screw (not shown) once the desired orientation is achieved. The basic functionality of this embodiment of the distractor apparatus 103 is the same as that described above with respect to the embodiment of the distractor apparatus 100 depicted in FIGS. 1-5.

While the embodiments of the distractor apparatus described in FIGS. 1-5 and 11 are described as having the distractor arm 122 substantially horizontally oriented, it should be understood that embodiments wherein the distractor arm 122 is vertically oriented are also contemplated.

Figure 6:
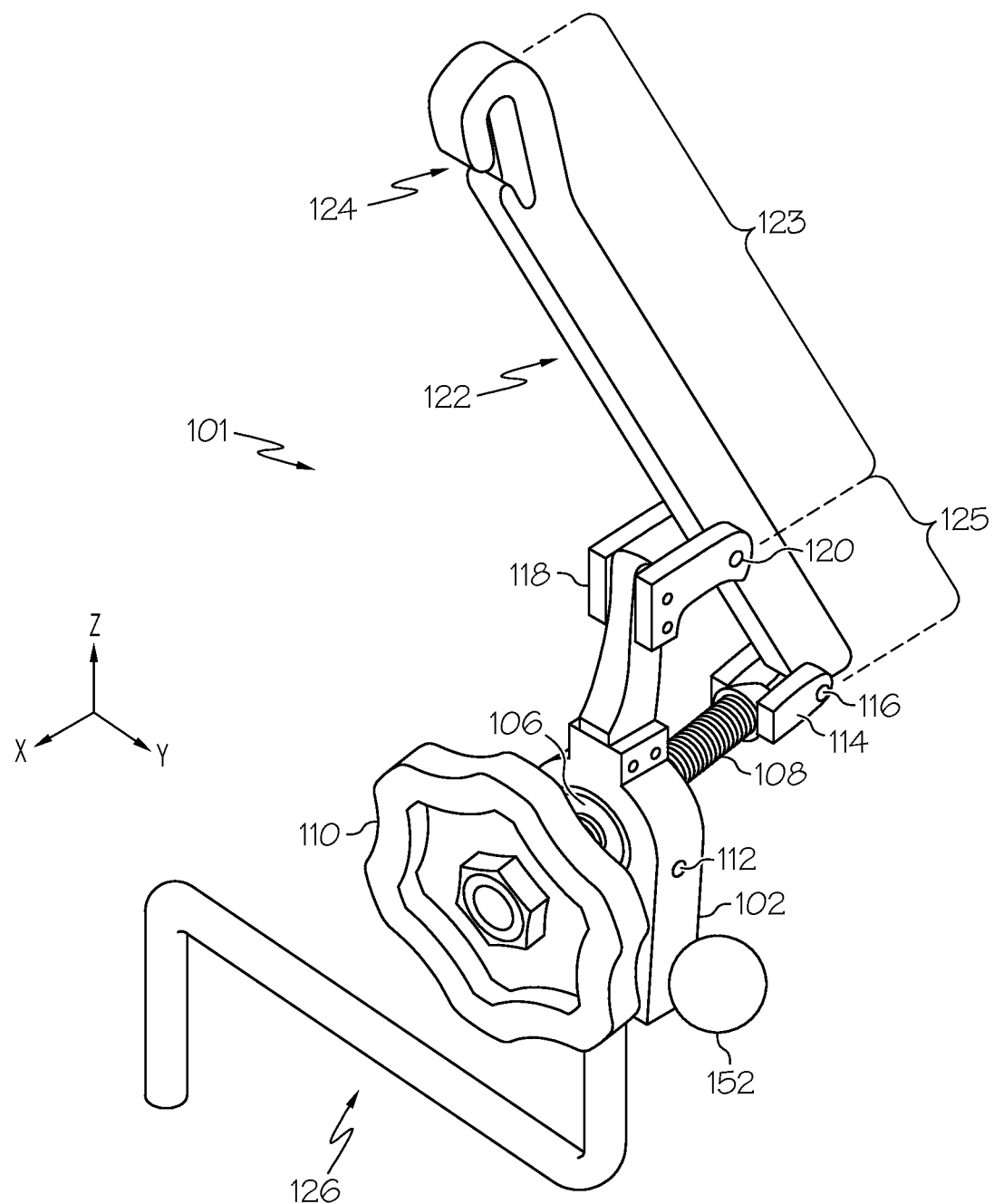
FIG. 6 schematically depicts a distractor apparatus according to another embodiment shown and described herein.
Figure 7:
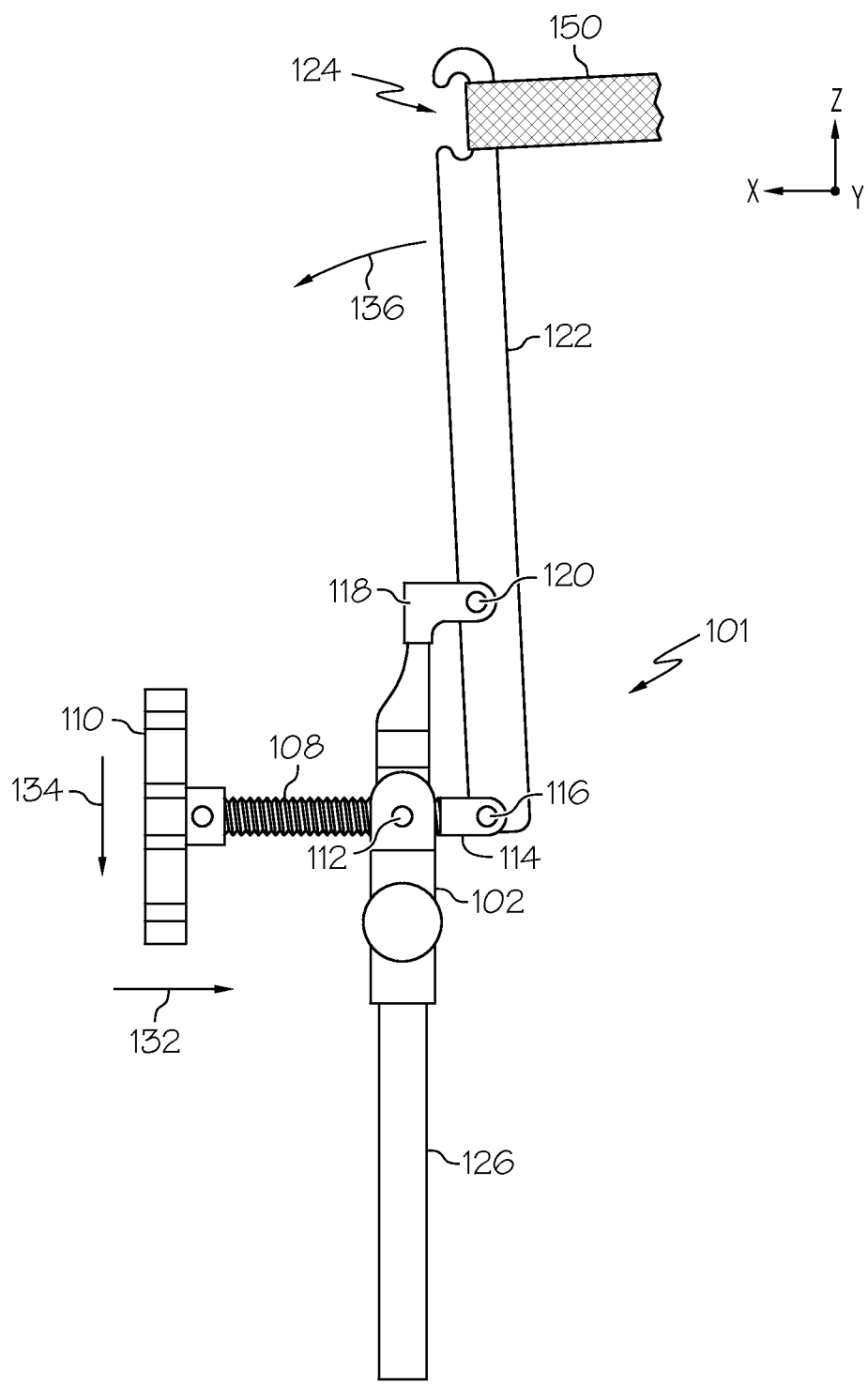
FIG. 7 schematically depicts the distractor apparatus of FIG. 6 being used to apply tension to a strap attached to the distractor apparatus.
Figure 8:
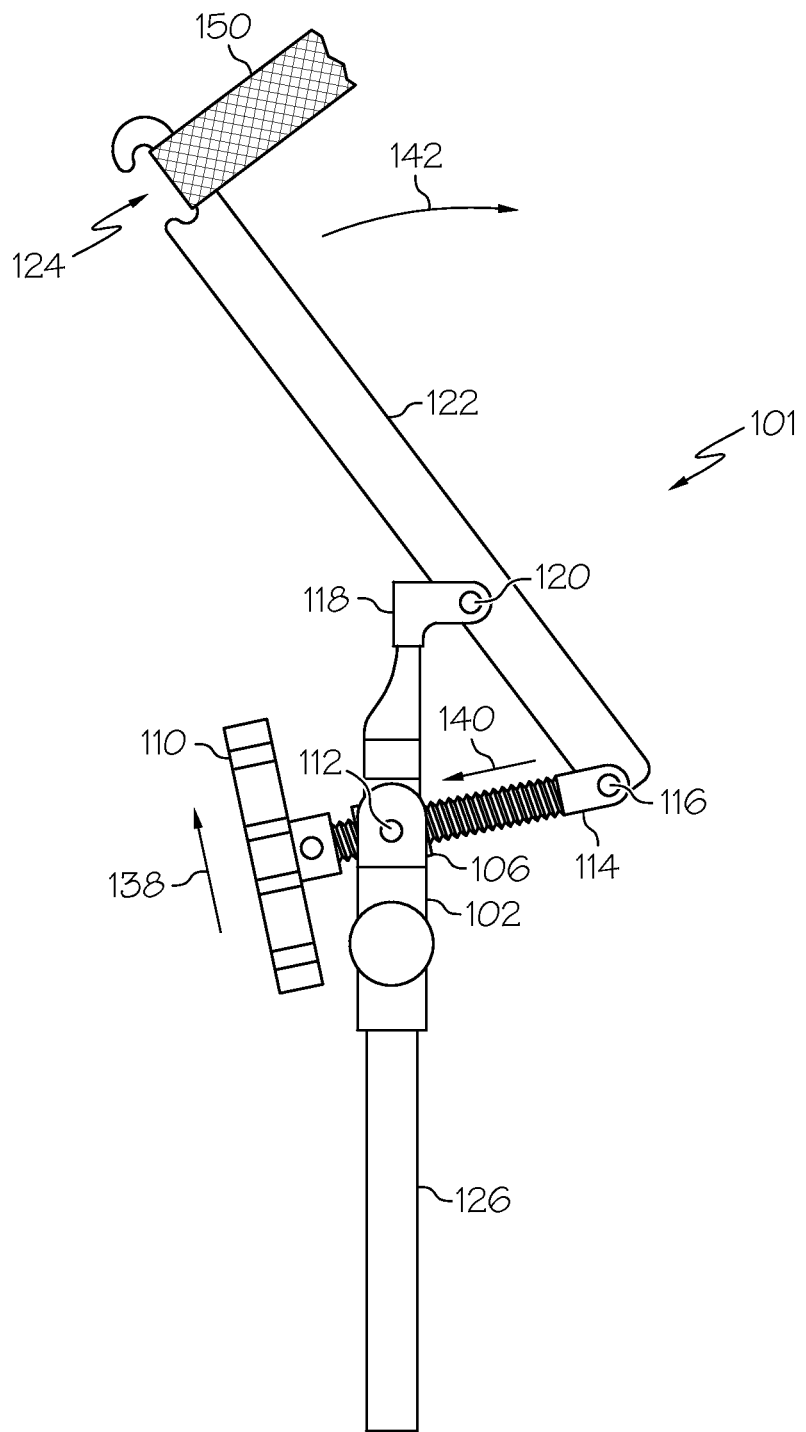
FIG. 8 schematically depicts an distractor apparatus of FIG. 6 being used to release tension applied to a strap attached to the distractor apparatus.

For example, referring to FIGS. 6-8, an embodiment of the distractor apparatus 101 in which the distractor arm 122 is substantially vertically oriented (i.e., the distractor arm is within +/−20 degrees of parallel with the y-z plane in the coordinate axes depicted in FIG. 7 when the control knob 110 is fully rotated in the slack direction, as shown in FIG. 7). In this embodiment the distractor apparatus 101 generally comprises a mounting body 102, a tensioning mechanism 109 and a distractor arm 122. The mounting body 102 is disposed on a first end of a support 126 which, in the embodiment shown in FIG. 6, is constructed of a cylindrical rod with multiple right angle bends such that the mounting body 102 is cantilevered with respect to at least a portion of the support 126. As described above with respect to FIG. 1, the second end of the support 126 may be coupled to a connector (not shown) to facilitate coupling the distractor apparatus 100 to an accessory rail (not shown) attached to a piece of medical equipment (not shown) such as, for example, a hospital bed or operating table. The mounting body 102 is rotatably positioned on the support 126 and fixed in place with the knob 152 attached to the set screw.

The mounting body 102 is formed with at least one opening in which a pivot nut 106 is positioned. Specifically, the pivot nut 106 is disposed in the mounting body and secured with pivot pins 112 (one shown in FIG. 6) such that the pivot nut 106 is free to rotate with respect to the mounting body 102 about an axis which is substantially parallel with the y-axis of the coordinate axes depicted in FIG. 6. The mounting body 102 also includes a body yoke 118.

The tensioning mechanism generally comprises a threaded rod 108, a control knob 110 and a rod yoke 114. The threaded rod 108 is threaded through the pivot nut 106 of the mounting body 102 such that a portion of the threaded rod 108 extends from either side of the mounting body. The control knob 110 is secured to a first end of the threaded rod 108 and the rod yoke 114 is secured to the second end of the threaded rod 108.

As described hereinabove, the distractor arm 122 is an elongated lever comprising a receiving hook 124 at a free end of the distractor arm 122 to facilitate attaching one or more accessories, such as a tensioning strap, tension gauge, or the like, to the distractor arm 122. The distractor arm 122 is pivotally coupled to the rod yoke 114 and the body yoke 118 such that the receiving hook 124 is pivotable with respect to the mounting body 102. Specifically, the body yoke 118 is coupled to the distractor arm 122 with pivot pin 120 between the ends of the distractor arm such that the distractor arm 122 is pivotable about the pivot pin 120. Similarly, the rod yoke 114 is coupled to an end of the distractor arm 122 with pivot pin 116. In the embodiment of the distractor apparatus 101 shown in FIGS. 6-8 the distractor arm 122 comprises a first portion 123 which extends from the pivot pin 120 to a free end of the distractor arm 122 and a second portion 125 which generally extends between pivot pin 116 and pivot pin 120. The first portion 123 is generally longer than the second portion 125 to increase the range of travel of the distractor arm 122 as well as the torque applied to a strap or other accessory connected to the receiving hook 124 of the distractor arm 122. In the embodiment of the distractor apparatus 100 depicted in FIG. 6 the distractor arm 122 is coupled to the body yoke 118 and the rod yoke 114 such that the distractor arm 122 is pivotable in the x-z plane of the coordinate axes of FIG. 6 with respect to the mounting body 102.

Referring now to FIGS. 7 and 8, the operation of the distractor apparatus 101 to apply a distraction force to a strap 150 positioned in the receiving hook 124 is schematically depicted. Referring to FIG. 7, a distraction force may be applied to the strap 150 by actuating the tensioning mechanism with control knob 110. Specifically, rotating the control knob 110 in a tensioning direction (which is the clockwise direction indicated by arrow 134 in this example) causes the threaded rod 108 to rotate in the pivot nut thereby advancing the threaded rod 108 in the direction indicated by arrow 132. As the threaded rod 108 advances it exerts a force on the distractor arm 122 through the rod yoke 114. The force applied to the distractor arm 122 causes the distractor arm 122 to rotate in a counter-clockwise direction in the body yoke 118 about the pivot pin 120 which, in turn, causes the receiving hook 124 of the distractor arm 122 to advance in the direction generally indicated by arrow 136, thereby applying a distraction force to the strap 150 and to a limb attached to the strap.

Moreover, as the distractor arm 122 is rotated about the pivot pin 120, the distractor arm 122 also pivots in the rod yoke 114 about the pivot pin 116 to accommodate for the rotation of the distractor arm 122. Further, as the distractor arm 122 rotates in the counter-clockwise direction, the distractor arm 122 exerts a torque on the threaded rod 108 causing the threaded rod 108 and the pivot nut 106 (not shown in FIG. 7) to rotate in the frame 104 about the pivot pin 112 in a counter-clockwise direction. The ability to rotate the threaded rod 108 and the pivot nut 106 in the mounting body 102 increases the maximum amount of travel of the threaded rod 108 as well as the amount of rotation of the distractor arm 122. FIG. 8 generally depicts the threaded rod 108 and the distractor arm 122 at maximum displacement when applying a distraction force to the strap 150.

Referring to FIG. 8, the distraction force applied to the strap 150 with the distractor apparatus 101 can be released by reversing the operation described above. Specifically, rotating the control knob 110 in a slack direction (which is the counter-clockwise direction indicated by arrow 138 in this example) causes the threaded rod 108 to rotate in the pivot nut 106 thereby advancing the threaded rod 108 in the direction indicated by arrow 140. As the threaded rod 108 advances it exerts a force on the distractor arm 122 through the rod yoke 114. The force applied to the distractor arm 122 causes the distractor arm 122 to rotate in a clockwise direction in the body yoke 118 about the pivot pin 120 which, in turn, causes the receiving hook 124 of the distractor arm 122 to advance in the direction generally indicated by arrow 142, thereby releasing the distraction force applied to the strap 150 and relaxing the distracting force on a limb attached to the strap.

As the distractor arm 122 is rotated about the pivot pin 120, the distractor arm 122 also rotates in the rod yoke 114 about the pivot pin 116 to accommodate for the rotation of the distractor arm. Further, as the distractor arm 122 rotates in the clockwise direction, the distractor arm exerts a torque on the threaded rod 108 causing the threaded rod 108 and the pivot nut 106 to rotate in the mounting body 102 about the pivot pin 112 in a clockwise direction. The control knob 110 may be rotated in the slack direction until a sufficient amount of slack is generated in the strap 150 and/or until the threaded rod reaches the maximum extent of travel in the direction of arrow 140.

Figure 9:
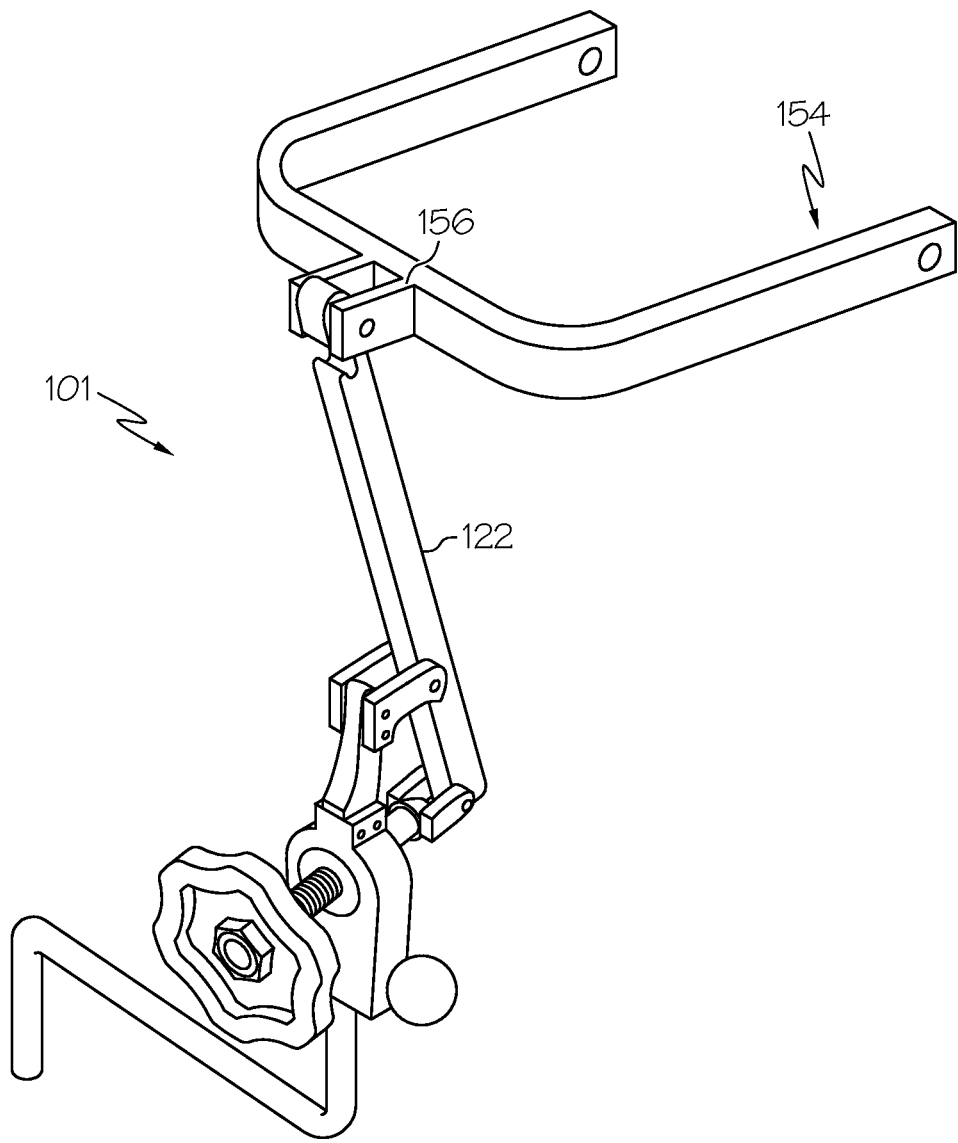
FIG. 9 schematically depicts the distractor apparatus of FIG. 6 with an accessory attached to the receiving hook of the distractor arm.
Figure 10A:
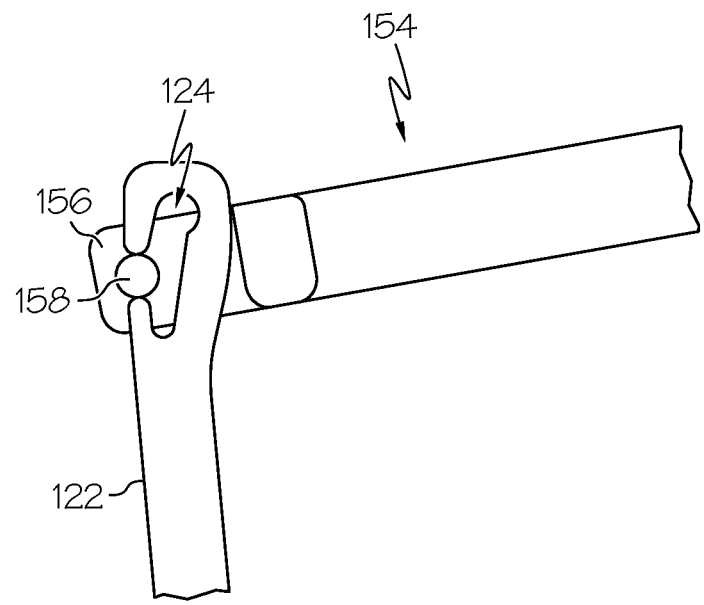
FIGS. 10A and 10B schematically depict the attachment of an accessory in the receiving hook of a distractor arm.
Figure 10B:
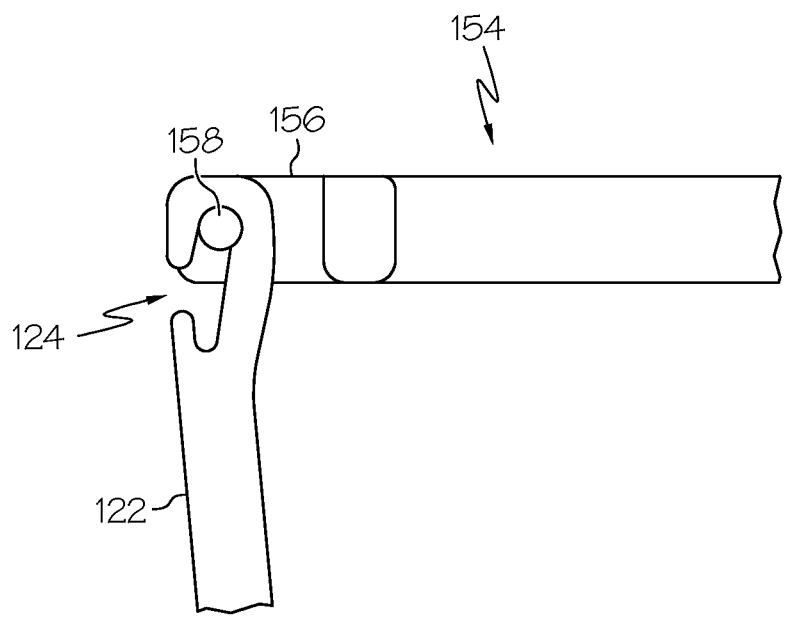

Referring now to FIGS. 9 and 10A-10B, the distractor arm 122 of the distraction apparatus has been described herein as comprising a receiving hook 124 for receiving a tensioning strap, a tension gauge for measuring a distraction force applied to an accessory and limb by the distraction apparatus, or another accessory. FIGS. 9 and 10A-10B depict the distractor apparatus 101 having an accessory, such as a skeletal bow 154 in this example, positioned in the receiving hook 124. Specifically, the skeletal bow 154 may be formed with a yoke 156 having a pivot pin 158 which bisects the yoke 156. The skeletal bow 154 may be attached to the distractor arm 122 by positioning the free end of the distractor arm 122 in the yoke 156 of the skeletal bow 154 such that the pivot pin 158 of the yoke 156 is engaged with the receiving hook 124 thereby facilitating rotation of the skeletal bow 154 in the receiving hook 124 about the pivot pin 158. In this manner, the distractor apparatus 101 may be utilized to exert a distraction force on the skeletal bow 154 in a similar manner as described hereinabove.

In the embodiments of the distraction apparatus described herein, the distraction mechanism utilizes a lever (i.e., the distractor arm) to transfer a distraction force generated along an axis of the tensioning mechanism (i.e., the tensioning axis) to a second axis (i.e., the effector axis) which is non-coaxial with the tensioning axis. For example, FIG. 3 depicts one embodiment of the distractor apparatus 100 in which the effector axis 302 is non-coaxial with the tensioning axis 301 throughout the range of motion of the tensioning mechanism and the distractor arm 122. Specifically, the distractor arm 122 is arranged such that the tension applied with the tensioning mechanism along the tensioning axis 301 is transferred to the effector axis 302 which is parallel (i.e., non-coaxial) with the tensioning axis 301. This facilitates positioning the tensioning mechanism of the distractor apparatus 100 off the long axis of the limb to which the distraction force is applied, thereby providing improved access to the limb, particularly from the area distal to the limb. In the embodiments of the distractor apparatus shown in FIGS. 1 and 6 the tensioning axis of the apparatus is substantially parallel to the effector axis throughout the range of motion of the tensioning mechanism and the distractor arm.

Other embodiments of tensioning apparatuses utilizing mechanisms to translate the tensioning force from a tensioning axis to an effector axis which is non-coaxial with the tensioning axis are also contemplated. For example, FIGS. 12A-12I depict various embodiments of distractor apparatuses in which the tensioning axis is non-coaxial with the effector axis such that the tensioning mechanism can be offset from the axis of the limb. Following are brief summaries of each contemplated embodiment.

Figure 12A:
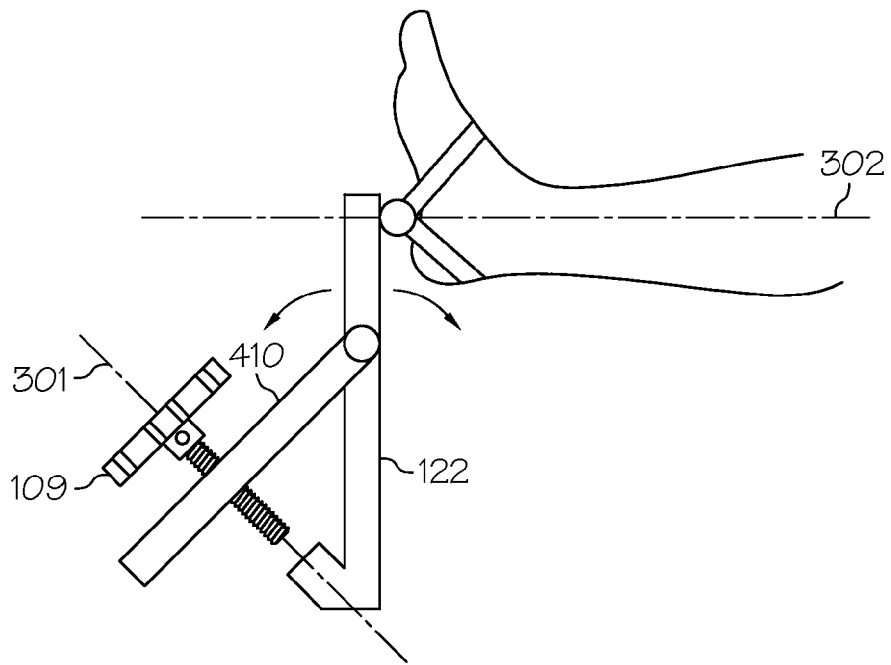

FIG. 12A depicts one embodiment of a distractor apparatus in which the tensioning apparatus has a tensioning axis 301 which is both non-parallel and non-coaxial with the effector axis 302. In this embodiment, the tensioning mechanism 109 is coupled to a strut 410 which is slidably and pivotally connected to the distractor arm. Rotating the tensioning mechanism 109 advances the strut along the tensioning mechanism which, in turn, pivots the distractor arm 122 thereby providing a distraction force along the effector axis 302.

Figure 12B:
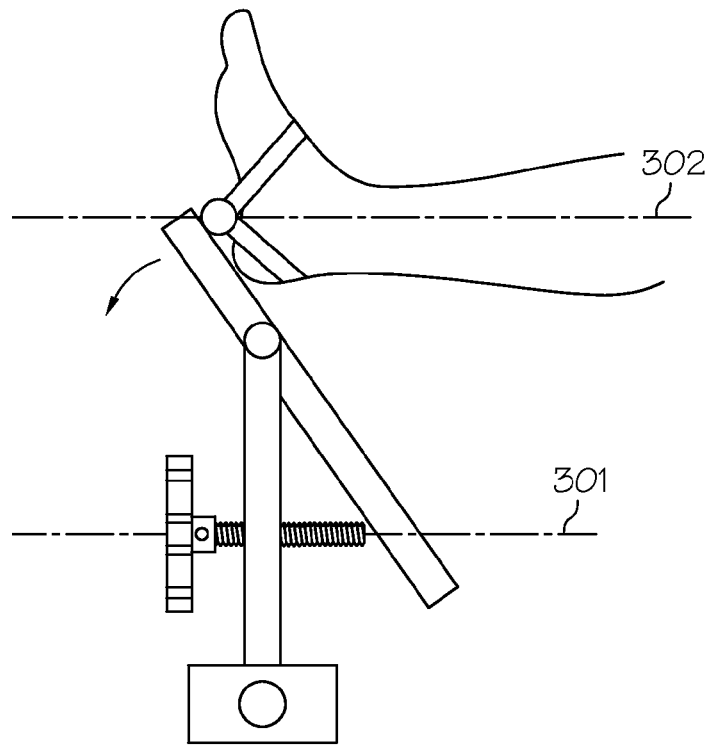

FIG. 12B depicts an embodiment of a distractor apparatus similar to that depicted in FIG. 4, described above.

Figure 12C:
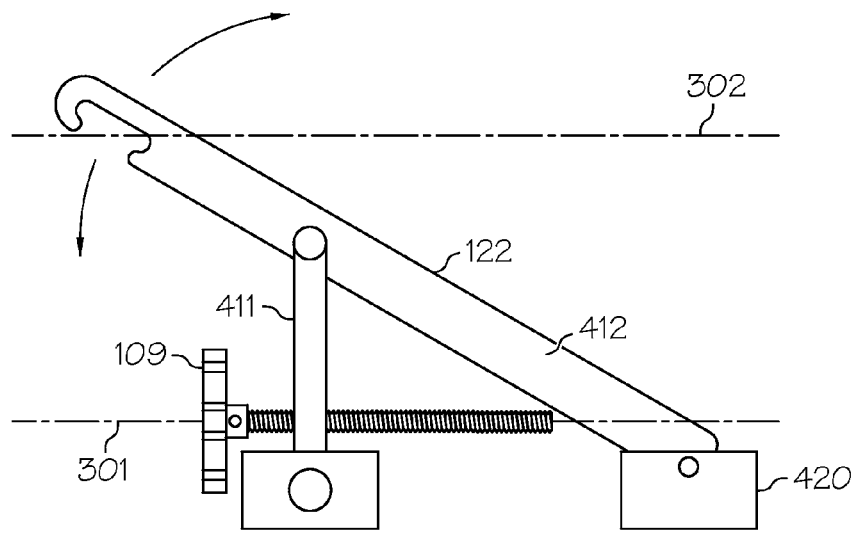

FIG. 12C depicts an embodiment of a distractor apparatus in which the distractor arm 122 is pivotally coupled to a sliding block 420. The tensioning mechanism 109 is slidably coupled to the distractor arm with strut 411 which rides in a channel 412 of the distractor arm 122. As the tensioning mechanism 109 is used to apply a distraction force along the tensioning axis 301, the rotation of the tensioning mechanism pushes the sliding block 420 in a direction away from the strut 411 which, in turn, causes the distractor arm 122 to slide and pivot on the strut 411 and pivot on the sliding block 420, thereby exerting a distraction force along the effector axis 302, which is substantially parallel with the tensioning axis 301.

Figure 12D:
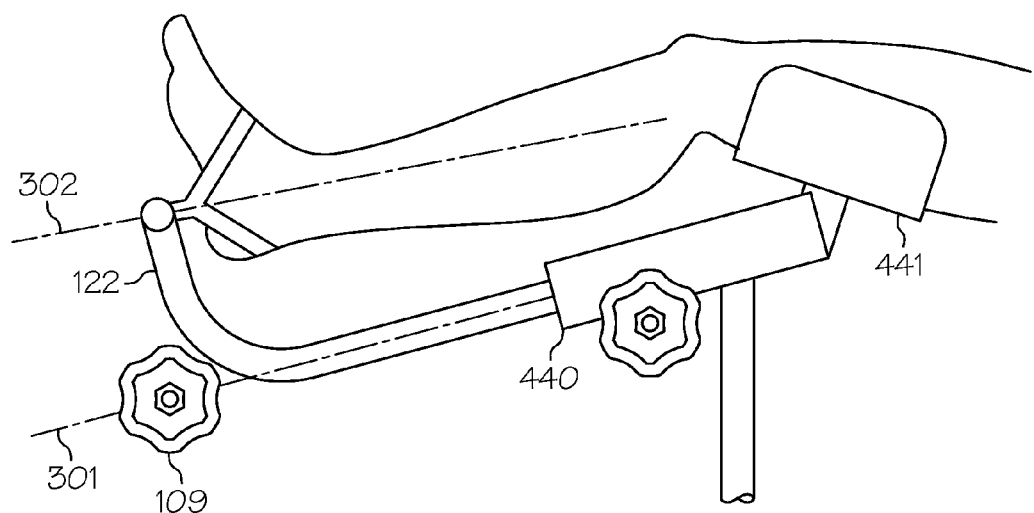

FIG. 12D depicts an embodiment a distractor apparatus in which the tensioning axis 301 and the effector axis 302 are substantially parallel. In this embodiment, the tensioning mechanism 109 is coupled to a telescoping mechanism 440 which may be used to extend or retract the distractor arm 122 which, in this embodiment, includes a right angle bend. The telescoping mechanism 440 may be coupled to a urology leg holder 441. As the tensioning mechanism 109 is used to apply a distraction force along the tensioning axis 301, the rotation of the tensioning mechanism causes the distractor arm 122 to extend from the telescoping mechanism 440, which translates the distraction force from the tensioning axis 301 to the effector axis 302.

Figure 12E:
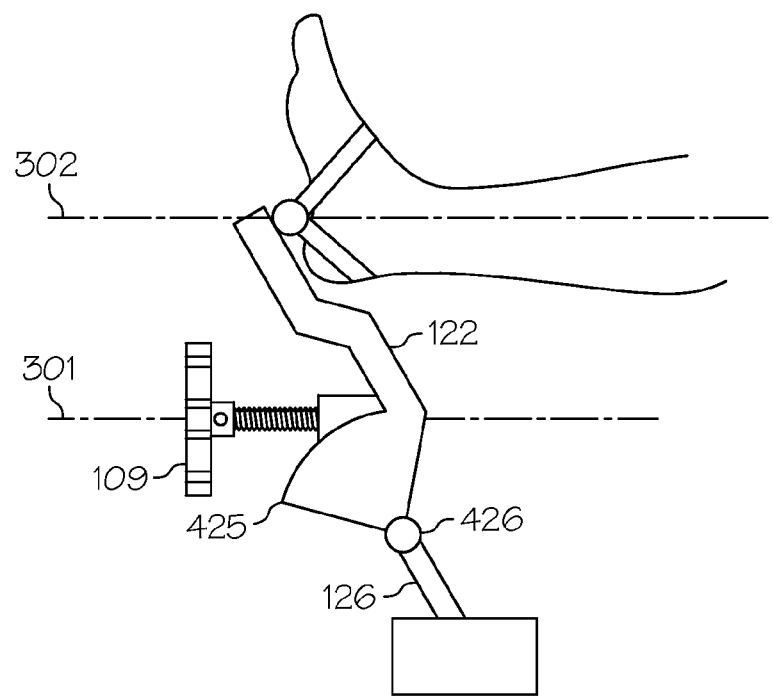
Figure 12F:
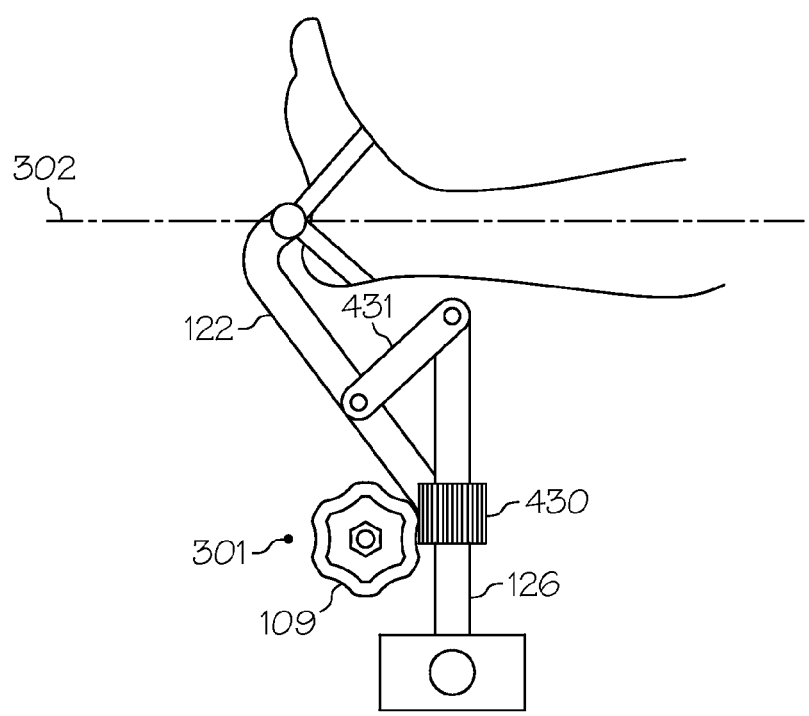
Figure 12G:
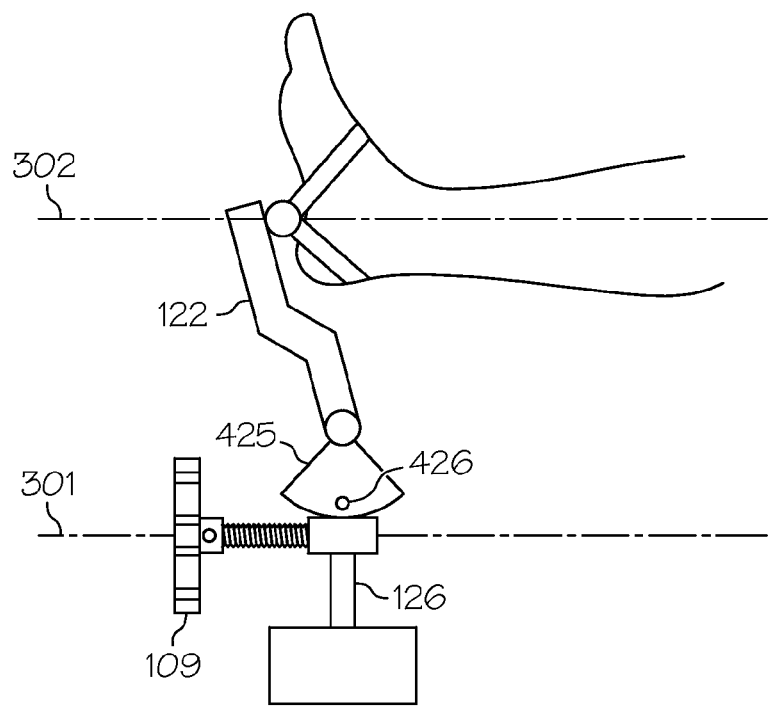

FIGS. 12E and 12G depict embodiments of distractor apparatuses in which the tensioning axis 301 and the effector axis 302 are substantially parallel. In these embodiments the distractor arm 122 is mounted on a support 126 and is pivotal on the support 126 about pivot point 426. The distractor arm 122 includes a rack 425 which engages with the tensioning mechanism 109 to pivot the distractor arm 122 about the pivot point 426. As the tensioning mechanism 109 is rotated to apply a distraction force along the tensioning axis 301, the distractor arm 122 is rotated about the pivot point 426 such that the distraction force is translated to the effector axis 302.

FIG. 12F depicts an embodiment of a distraction apparatus in which the tensioning axis 301 and the effector axis 302 are non-coaxial and non-parallel. In this embodiment, the distractor arm 122 is pivotally coupled to a strut 431 which, in turn, is pivotally coupled to a free end of the support 126. The distractor arm 122 is also coupled to a helical gear 430 which is slidably engaged with the support 126 and engaged with the tensioning mechanism 109. As the tensioning mechanism 109 is utilized to apply a distraction force along the tensioning axis 301, the position of the helical gear 430 on the support 126 is adjusted, thereby rotating the distractor arm 122 relative to the support 126 such that the distraction force is translated to the effector axis 302.

Figure 12H:
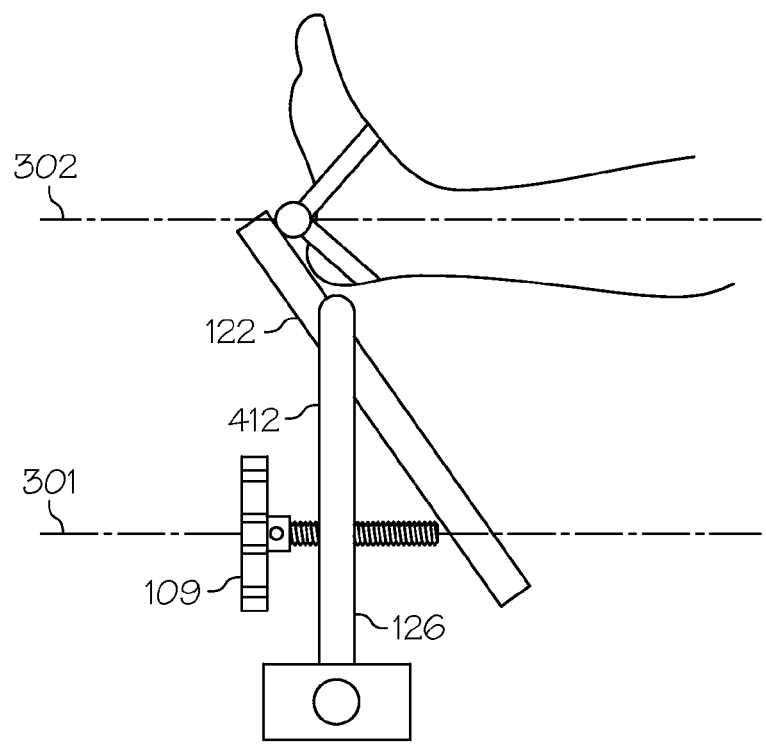
Figure 121:
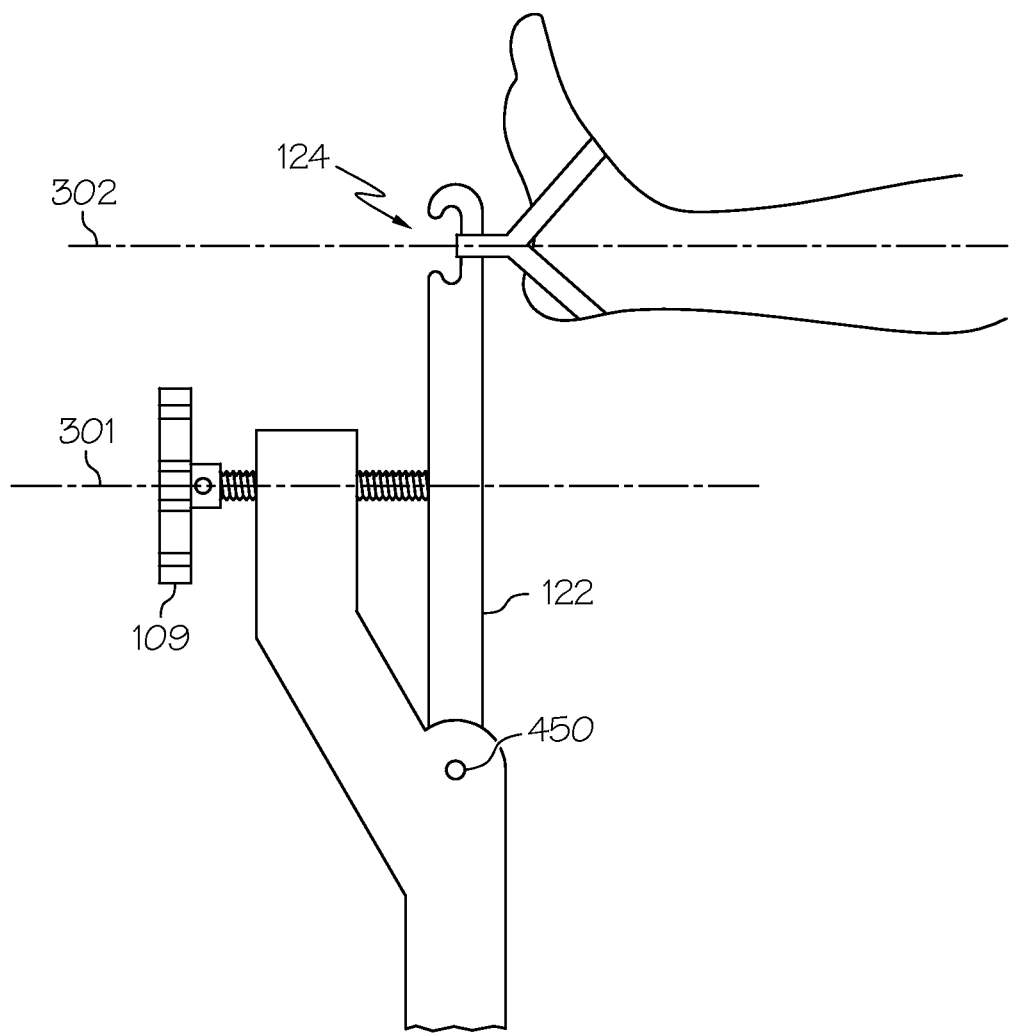

FIG. 12H depicts an embodiment of a distractor apparatus in which the tensioning axis 301 and the effector axis 302 are substantially parallel. In this embodiment the distractor arm 122 is pivotally mounted in a channel 412 in the support 126 such that the distractor arm 122 can slide along a length of the support 126 as well as pivot relative to the support 126. The tensioning mechanism 109 is also pivotally coupled to an end of the distractor arm 122. As a distraction force is exerted along the tensioning axis 301 with the tensioning mechanism 109, the rotation of the tensioning mechanism 109 pushes one end of the distractor arm 122 away from the support 126 thereby sliding the distractor arm 122 along the length of the support while simultaneously pivoting the free end of the distractor arm 122 away from the support 126 such that the distraction force is translated to the effector axis 302.

FIG. 12I depicts another embodiment of a distractor apparatus in which the tensioning axis 301 and the effector axis 302 are substantially parallel. This embodiment of the distractor apparatus is substantially similar to the embodiment shown in FIG. 4. However, in this embodiment, the pivot point 450 and the tensioning mechanism 109 are arranged such that the tensioning mechanism 109 is coupled to the distractor arm 122 between the pivot point 450 and the free end of the distractor arm 122 (i.e., the end comprising the receiving hook 124).

It should now be understood that the embodiments described herein generally relate to distractor apparatuses for use in applying a distraction force to a limb of a patient. These distractor apparatuses utilize a tensioning mechanism and lever (i.e., the distractor arm) to apply a distraction force to the limb of a patient and, as such, the mechanical advantage of the lever assists the operator in achieving the desired amount of distraction without the use of additional tools and/or apparatuses. Moreover, because the distractor apparatuses are capable of translating the distraction force from a tensioning axis to an effector axis which is non-coaxial with the tensioning axis, the distractor apparatuses may be positioned relative to a patient such that the tension mechanism does not substantially impede access to the distal areas of the limb.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A distractor apparatus comprising:
a mounting body;
a frame coupled to the mounting body, the frame comprising at least one pivot nut positioned in the frame such that the at least one pivot nut is pivotable with respect to the frame;

a tensioning mechanism coupled to the mounting body, the tensioning mechanism comprising a threaded rod having a control knob positioned on one end and a rod yoke positioned on an opposite end, wherein the threaded rod is engaged with the at least one pivot nut of the frame;

a body yoke coupled to the mounting body; and a distractor arm coupled to the tensioning mechanism and pivotally coupled to the mounting body for rotation relative to the mounting body, wherein:

a first end of the distractor arm is pivotally coupled to the rod yoke;

rotation of the tensioning mechanism applies a distraction force on the distractor arm;

a tensioning axis of the tensioning mechanism is non-coaxial and substantially parallel with an effector axis of the distractor arm throughout a range of motion of the tensioning mechanism and the distractor arm;

the distraction force applied to the distractor arm with the tensioning mechanism is translated from the tensioning axis to the effector axis through the distractor arm; and the body yoke is pivotally coupled to the distractor arm between a free end and the first end such that rotation of the tensioning mechanism pivots the distractor arm in the body yoke with respect to the mounting body and the distraction force applied along the tensioning axis of the tensioning mechanism is translated through the distractor arm to the effector axis of the distractor arm, wherein the tensioning axis is non-coaxial with the effector axis.

2. The distractor apparatus of claim 1, wherein the frame and the body yoke are rotatable with respect to the mounting body.

3. A distractor apparatus comprising:

a mounting body, the mounting body comprising a body yoke and a pivot nut positioned in the mounting body and pivotable with respect to the mounting body;

a tensioning mechanism coupled to the mounting body, wherein the tensioning mechanism is threadably engaged with the pivot nut, the tensioning mechanism comprising a threaded rod having a control knob positioned on one end and a rod yoke positioned on an opposite end; and a distractor arm coupled to the tensioning mechanism and pivotally coupled to the mounting body for rotation relative to the mounting body, wherein:

a first end of the distractor arm is pivotally coupled to the rod yoke and the body yoke is pivotally coupled to the distractor arm between the first end and a free end of the distractor arm;

rotation of the tensioning mechanism applies a distraction force on the distractor arm to rotate the distractor arm in the body yoke thereby pivoting the distractor arm with respect to the mounting body such that the distraction force applied to the distractor arm with the tensioning mechanism along a tensioning axis of the tensioning mechanism is translated from the tensioning axis to an effector axis through the distractor arm; and the tensioning axis of the tensioning mechanism is non-coaxial and substantially parallel with the effector axis of the distractor arm.

4. The distractor apparatus of claim 3, further comprising a support, wherein the mounting body is coupled to the support.

5. The distractor apparatus of claim 4, wherein the mounting body is cantilevered on the support.

6. The distractor apparatus of claim 3, further comprising a receiving hook disposed in the free end of the distractor arm and an accessory removably coupled to the receiving hook wherein the accessory is at least one of a tensioning strap, a tension gauge, or a skeletal bow.

7. A distractor apparatus for applying a distraction force to a limb of a patient, the distractor apparatus comprising:

a mounting body comprising a body yoke;

a frame coupled to the mounting body, the frame comprising at least one pivot nut positioned in the frame such that the at least one pivot nut is pivotable with respect to the frame;

a tensioning mechanism threadably engaged with the at least one pivot nut, the tensioning mechanism comprising a threaded rod having a control knob positioned on one end and a rod yoke positioned on an opposite end;

a distractor arm comprising a receiving hook disposed in a free end of the distractor arm, wherein:

a first end of the distractor arm opposite the free end is pivotally coupled to the rod yoke;

the body yoke is pivotally coupled to the distractor arm between the free end and the first end; and rotation of the tensioning mechanism pivots the distractor arm in the body yoke with respect to the mounting body such that the distraction force applied along a tensioning axis of the tensioning mechanism is translated through the distractor arm to an effector axis of the distractor arm, wherein the tensioning axis is non-coaxial and substantially parallel with the effector axis.

8. The distractor apparatus of claim 7, wherein the frame and the body yoke are rotatable with respect to the mounting body.

9. The distractor apparatus of claim 7, wherein the frame and the body yoke are rotatably coupled to the mounting body with an axle which extends from the frame, through the mounting body and into the body yoke.

10. The distractor apparatus of claim 9, wherein the mounting body further comprises a knob coupled to a set screw positioned in the mounting body such that rotation of the knob engages the set screw with the axle.

11. The distractor apparatus of claim 9, wherein:

the axle comprises at least one groove; and the mounting body further comprises a keeper having at least one lobe for engaging with the at least one groove of the axle, wherein the keeper is positioned in the mounting body and biased into engagement with the axle such that the at least one lobe is engaged with the at least one groove of the axle.

12. The distractor apparatus of claim 11, further comprising a knob coupled to the keeper, wherein depressing the knob disengages the keeper from the axle.

13. The distractor apparatus of claim 7, wherein the distractor arm comprises a first portion and a second portion and the second portion is shorter than the first portion.

14. The distractor apparatus of claim 13, wherein the body yoke is pivotally coupled to the distractor arm at a transition from the first portion to the second portion and the first end of the distractor arm in the second portion of the distractor arm.

15. The distractor apparatus of claim 7, further comprising a support, wherein the mounting body is coupled to the support.

16. The distractor apparatus of claim 15, further comprising a connector attached to the support such that the support and the connector are rotatable with respect to each other.

17. The distractor apparatus of claim 7, further comprising an accessory removably coupled to the receiving hook.

18. The distractor apparatus of claim 17, wherein the accessory is at least one of a tensioning strap, a tension gauge, or a skeletal bow.

\* \* \* \* \*